United States Patent [19]
Goschke

[11] 3,973,022
[45] Aug. 3, 1976

[54] QUINOLINEACETIC ACID COMPOSITIONS

[75] Inventor: Richard Goschke, Bottmingen, Switzerland

[73] Assignee: Ciba-Geigy Corporation, Ardsley, N.Y.

[22] Filed: Apr. 29, 1975

[21] Appl. No.: 573,274

Related U.S. Application Data

[62] Division of Ser. No. 337,998, March 5, 1973, Pat. No. 3,897,436.

[30] Foreign Application Priority Data

Mar. 10, 1972  Switzerland............. 3549/72
Jan. 29, 1973  Switzerland............. 1230/73

[52] U.S. Cl. ............................................. 424/258
[51] Int. Cl.² .......................................... A61K 31/47
[58] Field of Search ................................ 424/258

*Primary Examiner*—Stanley J. Friedman
*Attorney, Agent, or Firm*—Joseph G. Kolodny; Theodore O. Groeger; John J. Maitner

[57] ABSTRACT

Compounds of the formula

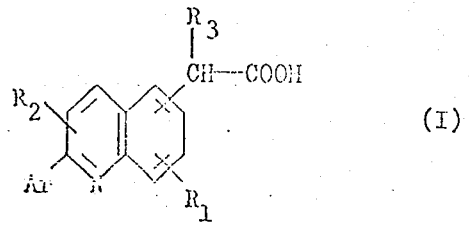

wherein Ar denotes an optionally substituted phenyl group or hetero-aromatic group with 5 or 6 ring members wherein the atom directly bonded to the quinoline ring is a carbon atom, $R_1$ represents hydrogen, halogen, lower alkyl, lower alkoxy or trifluoromethyl and $R_2$ and $R_3$ independently of one another denote hydrogen or a lower alkyl group, esters and amides of these carboxylic acids or salts of such compounds, have anti-inflammatory and analgesic activity; they are active ingredients of pharmaceutical compositions and can be used for the relief and removal of pain as well as for the treatment of rheumatic, arthritic and other inflammatory complaints; an illustrative example is α-methyl-2-(2-thienyl)-6-quinolineacetic acid.

18 Claims, No Drawings

QUINOLINEACETIC ACID COMPOSITIONS

CROSS-REFERENCE TO RELATED APPLICATION

This is a division of application Ser. No. 337,998, filed Mar. 5, 1973, (now U.S. Pat. No. 3,897,436).

The invention relates to new substituted quinolineacetic acids, their functional derivatives and salts, processes for the manufacture of these compounds, pharmaceutical compositions which contain these compounds, and their use.

The invention in particular relates to quinolineacetic acid compounds of the formula

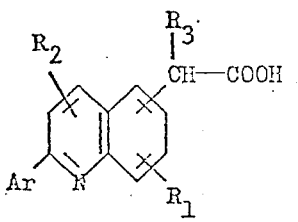

(I)

wherein Ar denotes an optionally substituted phenyl group or hetero-aromatic group with 5 or 6 ring members wherein the atom directly bonded to the quinoline ring is a carbon atom, $R_1$ represents hydrogen, halogen, lower alkyl, lower alkoxy or trifluoromethyl and $R_2$ and $R_3$ independently of one another denote hydrogen or a lower alkyl group, esters and amides of these carboxylic acids or salts of such compounds, and processes for their manufacture.

The term "lower" which is used in the preceding and following text in conjunction with organic radicals, groups or compounds denotes that organic radicals, groups and compounds designated in this way above all contain up to 7, preferably up to 4, carbon atoms.

A lower alkyl radical is, for example, a methyl, ethyl, n-propyl, isopropyl, n-butyl, isobutyl, sec.-butyl, tert.-butyl, n-pentyl, isopentyl, neopentyl, n-hexyl, isohexyl, n-heptyl or isoheptyl radical.

A lower alkoxy radical is, for example, a methoxy, ethoxy, n-propoxy, isopropoxy, n-butoxy, sec.-butoxy, t.-butoxy, n-pentoxy, isopentoxy, neopentoxy, n-hexoxy, isohexoxy, n-hexoxy or isohexoxy radical.

A hetero-aromatic group Ar contains, for example, in addition to the ring carbon atoms 1 or more, preferably 1, nitrogen or sulphur atoms as ring members. Particularly preferred hetero-aromatic groups are pyridyl groups, for example 2-, 3- or 4-pyridyl groups, or thienyl groups, such as 2- or 3-thienyl groups. A phenyl group or hetero-aromatic group can optionally possess one or more, preferably 1 or 2, identical or different substituents. Such substitutents are, for example, lower alkyl groups, such as those mentioned above, free, etherified or esterified hydroxyl groups, such as lower alkoxy groups, for example methoxy, ethoxy, n-propoxy, isopropoxy, n-butoxy or isobutoxy groups, or halogen atoms, for example fluorine, chlorine, bromine or iodine atoms, trifluoromethyl groups, nitro groups, amino groups, preferably di-lower alkylamino groups, for example dimethylamino, N-ethyl-N-methylamino, diethylamino, di-n-propylamino, di-isopropylamino, di-n-butylamino or di-isobutylamino groups, or lower alkanoylamino groups, for example acetylamino or pivaloylamino groups.

The radical $R_1$ is preferably hydrogen but can also represent lower alkyl, for example methyl or ethyl, lower alkoxy, for example methoxy or ethoxy, trifluoromethyl or halogen, for example fluorine, chlorine or bromine.

Examples of esters of acids of the formula I are lower alkyl esters, wherein lower alkyl has the abovementioned meaning.

Amides of acids of the formula I are optionally substituted amides, such as mono- or di-lower alkylamides, wherein lower alkyl has the abovementioned meaning, and also hydroxamic acids.

By salts of the compounds of the formula I and their functional derivatives there are above all understood salts of the acid compounds which fall under the definition, such as the free carboxylic acids, and also the corresponding hydroxamic acids with bases, as well as acid addition salts.

Salts of the acids which fall under the present invention are, for example, alkali metal salts, alkaline earth metal salts or earth metal salts, such as sodium salts, potassium salts, lithium salts, magnesium salts, calcium salts or aluminium salts, and also ammonium salts, for example with ammonia, with lower alkylamines which are optionally substituted, for example by hydroxyl or phenyl, such as with ethylamine, 2-aminoethanol, benzylamine, diethanolamine, 2-dimethylamino ethanol, trimethylamine or triethylamine, with lower alkylenediamines, such as ethylenediamine, with procaine and with cyclic lower alkyleneamines, wherein a carbon atom can optionally be replaced by a heteroatom, such as oxygen, such as pyrrolidine, piperidine and morpholine.

Acid addition salts, such as pharmaceutically usable non-toxic acid addition salts, are, for example, salts with inorganic acids, such as hydrochloric acid, hydrobromic acid, sulphuric acid, phosphoric acid, nitric acid or perchloric acid, or with organic acids, especially organic carboxylic acids or sulphonic acids, such as lower alkanemonocarboxylic or lower alkanedicarboxylic or lower alkenemonocarboxylic or lower alkenedicarboxylic acids which are optionally substituted, for example by hydroxyl, oxo or phenyl, for example formic acid, acetic acid, propionic acid, succinic acid, glycollic acid, lactic acid, malic acid, tartaric acid, citric acid, ascorbic acid, maleic acid, hydroxymaleic acid, pyruvic acid or phenylacetic acid, benzoic acids which are optionally substituted, for example by amino or hydroxyl, for example benzoic acid, 4-aminobenzoic acid, anthranilic acid, 4-hydroxybenzoic acid, salicylic acid and aminosalicylic acid, and also embonic or nicotinic acid, as well as optionally substituted lower alkanesulphonic acids or lower alkenesulphonic acids, such as methanesulphonic acid, ethanesulphonic acid, hydroxyethanesulphonic acid and ethylenesulphonic acid, or benzenesulphonic acids which are optionally substituted, for example by halogen or lower alkyl, such as benzenesulphonic acid, halogenobenzenesulphonic acid and toluenesulphonic acid.

The compounds according to the invention possess valuable pharmacological properties, especially an anti-inflammatory and analgesic activity, as well as a favourable therapeutic index. The anti-inflammatory activity manifests itself, for example, in rats in the kaolin paw oedema test, according to L. Riesterer and R. Jaques, Helv. physiol. pharmakol. Acta 25, 156 (1967), in which the compounds according to the invention possess a detectable action on peroral administration of about 10 to 100 mg/kg.

The analgesic effects can be demonstrated, for example, with the aid of the writhing test in mice, such as according to the method developed by Siegmund et al., Proc.Soc.Exptl. Biol.Med., volume 95, page 729 (1957), at oral doses of about 10 to about 100 mg/kg.

The compounds of the present invention can therefore be used as analgesic, especially as anti-inflammatory, agents, above all for the treatment of arthritic symptoms. They can also be used as intermediate products in the manufacture of other pharmacologically active, valuable compounds.

Preferred compounds of the present invention are those of the formula I in which Ar denotes a phenyl group which is optionally substituted by lower alkyl or lower alkoxy with at most 4 carbon atoms, fluorine, chlorine, bromine or trifluoromethyl, a thienyl group or pyridyl group, $R_1$ denotes hydrogen or chlorine, $R_2$ and $R_3$ independently of one another denote hydrogen or lower alkyl with at most 4 carbon atoms, and one of the groups —$CH(R_3)COOH$ and $R_1$ occupies the 6-position and the other the 8-position and the group $R_2$ occupies the 4-position, their lower alkyl esters with at most 4 carbon atoms, unsubstituted and N-hydroxy-substituted amides thereof, and salts of these compounds.

Particularly preferred compounds of the formula I are those wherein Ar denotes a phenyl group which is optionally substituted by fluorine, chlorine, methyl, methoxy or trifluoromethyl, or a thienyl group, $R_1$ denotes hydrogen, $R_2$ denotes hydrogen or methyl in the 4-position and $R_3$ denotes hydrogen or methyl and wherein the —$CH(R_3)COOH$ group occupies the 6-position, methyl esters of these acids and their salts with bases.

The compounds of the present invention are obtained according to methods which are in themselves known. Thus they can be formed, for example, if in a compound of the formula

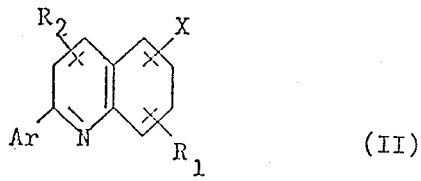

(II)

wherein X represents a radical which can be converted into an optionally esterified or amidised group of the formula —$CH(R_3)$—$C(=O)$—$OH$ (IIa), X is converted into an optionally esterified or amidised group of the formula —$CH(R_3)$—$C(=O)$—$OH$ (IIa) and, if desired, a resulting compound is converted into another compound within the framework which has been defined.

Thus it is possible, in a compound of the formula II, wherein X represents a radical of the formula —$CH(R_3)$—$X_1$ (IIb), wherein $X_1$ represents a radical which can be converted into the optionally esterified or amidised carboxyl group, to convert $X_1$ into an optionally esterified or amidised carboxyl group. A group $X_1$ is, for example, a nitrile group, an optionally substituted thiocarbamoyl group, an etherified hydroxyl or mercaptoformimidoyl group or a trihalogenomethyl or tri-lower alkoxymethyl group.

An optionally substituted thiocarbamoyl group is, for example, a N-lower alkylthiocarbamoyl or N,N-di-lower alkylthiocarbamoyl group, and also a lower alkyleneamino-thiocarbonyl group, wherein the carbon atoms of the lower alkylene radical can preferably be interrupted by a nitrogen or a sulphur atom, but especially an oxygen atom, such as, for example, a morpholinethiocarbonyl group. An etherified hydroxy-formimidoyl group (that is to say a O-etherified group of the formula HO—$C(=NH)$—) is in particular lower alkoxyformimidoyl, for example methoxy-formimidoyl or ethoxy-formimidoyl, whilst an etherified mercapto-formimidoyl group (that is to say a S-etherified group of the formula HS—$C(=NH)$—) in particular represents lower alkylthio-formimidoyl, for example methylthio-formimidoyl or ethylthio-formimidoyl. A trihalogenomethyl group is, for example, trichloromethyl and a tri-lower alkoxymethyl group is, for example, trimethoxymethyl or triethoxymethyl.

The conversion of a group $X_1$ into an optionally esterified or amidised carboxyl group can be effected by hydrolysis.

The hydrolysis is advantageously carried out in a basic or acid medium. Bases are, for example, inorganic bases, such as alkali metal hydroxides or alkaline earth metal hydroxides, for example sodium hydroxide or calcium hydroxide, and also salts of these hydroxides with weak acids, such as carbonic acid, for example the corresponding carbonates and bicarbonates. It is also possible to use organic bases, preferably strong organic bases, such as quaternary ammonium hydroxides, for example quaternary lower alkylammonium hydroxides, such as tetramethylammonium hydroxide and tetra-n-butylammonium hydroxide, as well as their salts with weak acids, such as carbonic acid, for example the corresponding carbonates and bicarbonates, and also tertiary amines, such as tert.-lower alkylamines, for example trimethylamine, diisopropylethylamine, dicycloalkyl-lower alkylamines, such as dicyclohexylethylamine, nitrogen-containing heterocyclics, such as N-lower alkylpiperidines and alkylmorpholines, for example N-methylpiperidine or N-methylmorpholine, and also basic ion exchangers.

The basic hydrolysis is carried out in water, advantageously in a mixture of water and a solvent which is inert under the reaction conditions and is miscible with water. Such solvents are, for example, water-miscible ether-like liquids, such as dioxane, ethylene glycol lower alkyl ethers, such as ethylene glycol monomethyl ether or dimethyl ether, ethylene glycol monoethyl ether or diethyl ether, diethylene glycol lower alkyl ethers, such as diethylene glycol monomethyl ether or dimethyl ether, and diethylene glycol monoethyl ether or diethyl ether, liquid alcohols, such as lower alkanols, for example methanol or ethanol or sulphoxides, such as di-lower alkylsulphoxides or lower alkylenesulphoxides, for example dimethylsulphoxide.

The reaction is preferably carried out at elevated temperature, for example between about 20°C and 150°C, if appropriate in a closed vessel.

The acid hydrolysis is advantageously carried out in the presence of strong acids. Strong acids are, for example, mineral acids, for example hydrogen halide acids, such as hydrochloric acid and hydrobromic acid, inorganic oxygen acids, such as sulphuric acid, phosphoric acid or perchloric acid, strong organic acids, for example aliphatic or aromatic sulphonic acids such as optionally halogen-substituted lower alkanesulphonic acids, for example methanesulphonic acid or trifluoromethanesulphonic or trichloromethanesulphonic acid, or benzenesulphonic acids which are optionally substituted, for example by alkyl, such as methyl, phenyl, nitro or halogen, such as chlorine or bromine, for example benzenesulphonic acid, p-toluenesulphonic acid, p-diphenylsulphonic acid, p-nitrobenzenesulphonic acid or p-bromobenzenesulphonic acid. In the acid hydrolysis, solvents used are water or a mixture of water and a solvent which is inert under the reaction conditions and is water-miscible. Such solvents are above all lower alkanecarboxylic acids, such as acetic acid, and also the above-mentioned water-miscible ether-like liquids.

According to a preferred method of carrying out the reaction, a compound of the formula II, wherein X corresponds to the formula IIb and $X_1$ represents, for example, the nitrile group or a trichloromethyl group, is first treated with a liquid acid which comes under the abovementioned acids, for example with sulphuric acid, in the presence or absence of a diluent, for example of a lower alkanecarboxylic acid, such as acetic acid, and the resulting mixture is decomposed with water.

The reaction is advantageously carried out at normal or elevated temperature, preferably between about 20° and 120°C.

The hydrolysis of the nitriles and thioamides to the corresponding carboxylic acids takes place via the corresponding amides as intermediate stages; these amides can be isolated if desired. The hydrolysis of the imidoesters and orthoesters to the acids takes place via the corresponding esters as intermediate stages which can also, if desired, be isolated.

The compounds of the formula I, as well as their esters or amides, and also salts of such compounds, can also be manufactured if a compound of the formula II, wherein X represents a group of the formula $-CH(R_3)-X_2$ (IIc), in which $X_2$ denotes a metallic radical, is treated with a functional derivative of carbonic acid.

A metallic radical is, for example, an alkali metal atom or a substituted alkaline earth metal atom, zinc atom or cadmium atom, such as a halogenomagnesium group as well as a lower alkyl-zinc or lower alkyl-cadmium group, for example a methyl- or ethyl-zinc group or -cadmium group, but preferably the lithium atom or a chloromagnesium, bromomagnesium or iodomagnesium group.

Functional derivatives of carbonic acid are preferably its esters, for example lower alkyl esters thereof, such as diethyl carbonate, also halides, such as phosgene, carbamoyl halides, such as diethylcarbamoyl chloride, and especially the anhydride of carbonic acid, that is to say carbon dioxide. The reaction is advantageously carried out in a solvent, such as an inert organic solvent, for example an aliphatic or aromatic hydrocarbon, such as pentane, benzene or toluene, and also in hydrocarbon mixtures, such as petroleum ether or ligroin, but preferably in one of the abovementioned ether-like solvents. The reaction is carried out at lowered or elevated temperature, for example between above −80° and about +100°C, preferably between 0° and 40°C.

According to a further process variant, compounds of the present invention can be manufactured by treating a compound of the formula II, wherein X is a group of the formula $-CH(R_3)-X_3$ (IId), wherein $X_3$ represents an optionally etherified hydroxyl group, with carbon monoxide or with formic acid or with a reactive functional derivative thereof.

An etherified hydroxyl group $X_3$ is, for example, a lower alkoxy group, such as the methoxy group.

Reactive functional derivatives of formic acid are above all their esters, such as lower alkyl esters, for example formic acid methyl ester or formic acid ethyl ester and ortho-formic acid methyl ester and ethyl ester. The reaction can, for example, be carried out at high pressures and/or temperatures, for example at up to about 400 atmospheres and about 300°C, preferably in the presence of a heavy metal catalyst, such as a nickel salt or cobalt salt, or of a carbonyl derivative, thereof, without solvents or in water. In another process variant, the carbon monoxide, which can, if desired, be evolved from suitable reagents, such as formic acid in the presence of high-boiling mineral acids, such as sulphuric acid or phosphoric acid, can be used in the presence of these acids at lowered or elevated temperature, for example between about −10° and 200°C.

According to a further process variant, the compounds of the present invention can be manufactured by oxidising a compound of the formula II, wherein X represents a group of the formula $-CH(R_3)-CHO$ (IIe).

The oxidation can be carried out with the aid of standard oxidation methods, for example by treatment with oxygen (either in the pure form or in the form of air), preferably in the presence of a suitable catalyst, such as a silver catalyst, manganese catalyst, iron catalyst or cobalt catalyst, or with oxidising agents such as hydrogen peroxide, or a nitrogen oxide (nitric oxide), oxidising acids or salts thereof, such as hypohalous acids, periodic acid, nitric acid or percarboxylic acids or corresponding salts, such as alkali metal salts thereof, for example sodium hypochlorite or sodium periodate, peracetic acid, perbenzoic acid or monoperphthalic acid, heavy metal salts or oxides, such as alkali metal chromates, for example sodium chromate or potassium chromate, or alkali metal permanganates, for example sodium permanganate or potassium permanganate, chromium-III or copper-II salts, for example halides or sulphates, or silver, mercury, vanadium-V, chromium-VI or manganese-IV oxides, in an acid or alkaline medium. Additionally, the oxidation can be carried out electrochemically.

The oxidation is advantageously carried out in solvents which are stable towards the oxidising agents used, for example water or ketones, such as lower alkyl ketones, for example acetone or methyl ethyl ketone, lower alkanecarboxylic acids, such as acetic acid, hydrocarbons such as benzene, chlorinated hydrocarbons, such as chlorobenzene, carbon tetrachloride or tetrachloroethane and also nitrogen-containing heterocyclic compounds, such as pyridine. The reaction is carried out at lowered, normal or elevated temperature, for example between about −10° and about 100°C.

Aldehyde starting substances can be formed in situ, for example by starting from compounds which can be oxidised to the former, for example from appropriate halogenomethyl compounds of the formula II, wherein X represents a radical of the formula $-CH(R_3)-X_4$ (IIf), in which $X_4$ denotes, for example, halogenomethyl, and employing these in the oxidation reaction. In that case, the above aldehyde starting substances are obtained as intermediate products.

Compounds of the present invention can furthermore be obtained if in a compound of the formula II, wherein X denotes an optionally esterified or amidised group of the formula —C(=$R_3^o$)—C(=O)-OH (IIg), in which $R_3^o$ represents a lower alkylidene group, $R_3^o$ is reduced to a lower alkyl group.

The above reduction is carried out, for example, by treatment with a metal, for example with an alkali metal, such as sodium, in the presence of a proton donor, preferably a lower alkanol, such as ethanol but is preferably carried out with catalytically activated hydrogen, using as the catalyst a transition metal or transition metal derivative, such as nickel, platinum, platinum oxide or palladium, if desired on a neutral carrier, such as kieselguhr, calcium carbonate or animal charcoal. The hydrogenation is advantageously carried out in the presence of a solvent, for example water or an inert organic solvent, for example one of the abovementioned ether-like solvents, an alcohol, such as a lower alkanol, for example ethanol, an organic acid, such as a lower alkanecarboxylic acid, for example acetic acid, or an ester of such an acid, for example with lower alkanols, such as ethyl acetate, or a liquid amide, such as a di-lower alkylamide of a lower alkane-carboxylic acid, for example dimethylformamide or dimethylacetamide and, if desired, at elevated pressure, for example up to 50 atmospheres gauge, and/or whilst cooling or warming, for example between about 0° and 100°C.

According to a further process variant, the compounds of the present invention can be manufactured by decarboxylating a compound of the formula II, wherein X denotes an optionally esterified or amidised group of the formula —C($R_3$)—($X_5$)—C(=O)—OH (IIh), in which $X_5$ denotes a carboxyl group.

To carry out the decarboxylation a starting material is warmed in the presence or absence of a solvent and/or of a catalyst.

Solvents used are, in addition to water, organic solvents, preferably those of higher boiling point, such as alcohols, for example lower alkanols, such as ethanol, polyhydric alcohols, such as lower alkanediols or alkanetriols, for example glycerine or glycol, ether-like solvents, such as di-lower alkyl ethers, for example dibutyl ether, ethylene glycol mono- or di-lower alkyl ethers or diethylene-glycol mono- or di-lower alkyl ethers, such as ethylene glycol monomethyl ether, ethylene glycol dimethyl ether, diethylene glycol monomethyl ether or diethylene glycol dimethyl ether, or diaryl ethers, for example diphenyl ether, liquid nitrogen bases, such as lower alkylamines, for example triethylamine and ethyldiisopropylamine, dicycloalkyl-lower alkylamines, such as dicyclohexyl-methylamine, aryl-lower alkylamines, for example dimethylaniline, optionally substituted nitrogen-containing heterocyclic compounds, for example pyridine, picolines or collidines, and also quinoline, and liquid amides, such as di-lower alkylamides of lower alkanecarboxylic acids, for example dimethylformamide or dimethylacetamide. Copper of copper salts, such as copper-I chloride, can, for example, serve as catalysts. The reaction is carried out at elevated temperature, for example between about 50° and 250°C.

The compounds of the present invention can also be manufactured if a compound of the formula II, wherein X denotes a group of the formula —CH($R_3$)—$X_6$ (IIi), in which $X_6$ represents and optionally esterified carboxycarbonyl group, is decarbonylated. The decarbonylation can, for example like the above decarboxylation, be carried out at elevated temperature and preferably in the presence of a solvent.

According to a further process variant, the compounds of the present formula can also be manufactured if a compound of the formula II, wherein X represents a group of the formula —C(=O)—C($N_2$)—$R_3$ (IIk), is reacted with water, an alcohol, ammonia or an amine.

The above reaction is carried out in accordance with the Arndt-Eistert and Wolff method, preferably in the presence of a noble metal or of a noble metal salt as the catalyst, for example of copper or platinum or preferably of a silver salt, such as silver nitrate or silver oxide, or of a complex metal salt thereof with sodium thiosulphate. The reaction is preferably carried out in the presence of a solvent, advantageously in an excess of of the water, alcohol or amine required for the solvolysis, or of an inert diluent, such as an ether-like solvent, for example dioxane, a ketone, such as a lower alkylketone, for example acetone, a carboxylic acid, such as a lower alkanecarboxylic acid, for example acetic acid, or an amide, such as a di-lower alkylamide of a lower alkanecarboxylic acid, for example dimethylformamide or dimethylacetamide. The reaction is preferably carried out at normal or elevated temperature, for example between about 20° and 120°C.

According to a particularly advantageous embodiment, a solution of the diazoketone used as the starting material is slowly added to an aqueous solution of silver nitrate and sodium thiosulphate or to a suspension of silver oxide in an aqueous solution of sodium sulphate, with the temperature of the aqueous solution or suspension being about 60°–70°C. It is furthermore possible to treat a solution of the diazoketone in an alcohol, for example in a lower alkanol, at its boiling point, with freshly prepared silver oxide added in portions until no further nitrogen evolution is detectable.

The compounds of the present application can also be obtained if an aniline derivative of the formula

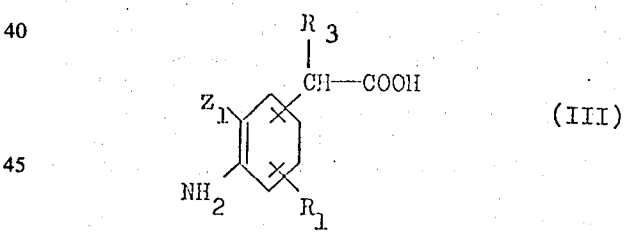

or an ester or an amide thereof with regard to the carboxyl group is condensed with a compound of the formula Ar—$Z_2$ (IV) in which $Z_1$ and $Z_2$ denote radicals which together with the aniline radical are capable of forming the desired quinoline ring and, if desired, a resulting compound is converted into another compound of the invention within the defined scope.

Thus, a compound of the formula III, wherein $Z_1$ denotes a hydrogen atom, can be condensed with a compound of the formula IV, wherein $Z_2$ presents a radical of the formula —CH=C($R_2'$)—C($R_2''$)=O (IVa), in which one of the groups $R_2'$ and $R_2''$ denotes hydrogen and the other corresponds to the definition of $R_2$ under the formula I, in accordance with the method of Doebner and Miller. The condensation is advantageously carried out in the presence of acids, such as of mineral acids, for example hydrogen halide acids, such as hydrochloric acid, oxygen acids, such as phosphoric acid or sulphuric acid, strong organic acids, such as optionally substituted lower alkylsulphonic acids or benzenesulphonic acids, such as toluene-sulphonic acid or trifluoromethanesulphonic acid, or of Lewis acids, such as, for example, halides, for example of zinc, and also of boron, aluminium, titanium, tin, phosphorus, antimony and iron, such as zinc chloride, boron trifluoride, aluminium chloride, titanium tetrachloride, tin tetrachloride, phosphorous pentachloride or antimony pentachloride or iron trichloride. The reaction is advantageously carried out in the presence of an oxidising agent, such as an organic nitro compound, for example an optionally substituted nitrobenzene, such as nitrobenzene or o-nitrobenzoic acid, of a transition metal salt of high oxidation level, for example a ferric salt, such as ferric chloride, of an oxidising acid, such as arsenic acid, or of a halogen, such as iodine. The reaction is preferably carried out in the absence of a diluent or in a liquid condensation agent as the solvent, and at elevated temperature, for example between about 50° and 250°C.

According to another process variant, compounds of the present invention can be obtained if a compound of the formula III, wherein $Z_1$ denotes a group of the formula —$COR_2'$ (IIIb), is condensed with a compound of the formula IV, wherein $Z_2$ is a group of the formula —$COOH_2R_2''$ (IVb), in which one of the groups $R_2'$ and $R_2''$ denotes hydrogen and the other corresponds to the definition of $R_2$ under the formula I, in accordance with Friehlander's method. The condensation agents used are the acid agents listed under the Doebner-Miller condensation, advantageously in the absence of a diluent or in an excess of the liquid condensation agent as solvent. Preferably, the reaction is carried out at elevated temperature, for example between about 50° and 250°.

According to a further process variant, compounds of the present invention can be obtained if a compound of the formula III, wherein $Z_1$ denotes a group of the formula —$CH_2$—$R_2'$ (IIIc), are condensed with a compound of the formula IV, wherein $Z_2$ denotes the radical of the formula —$C(=O)$—$C(R_2'')=O$ (IVc), in which one of the groups $R_2'$ and $R_2''$ denotes hydrogen and the other corresponds to the definition of $R_2$ under the formula I, according to Kulisch's method. The condensation can be carried out in the presence of the acid agents listed under the Doebner-Miller condensation, but advantageously strong bases are used as catalysts, for example the strong bases listed earlier, for example alkali metal hydroxides or alkali metal alcoholates such as alkali metal lower alkanolates, for example potassium hydroxide or potassium ethanolate. The acid condensation is advantageously carried out without solvents or in a liquid condensation agent as the solvent whilst the base-catalysed condensation is preferably carried out in a solvent, for example in water, or in organic solvents, such as lower alkanols, for example ethanol, and also in ether-like solvents, such as ethylene glycol lower alkyl ethers, for example ethylene glycol monomethyl ether, preferably at an elevated temperature, for example between about 50° and 250°.

Resulting compounds can be converted into one another in a manner which is in itself known. Thus, for example, resulting free acids can be esterified using alcohols, in the presence of esterifying agents, such as strong acids, for example hydrogen halide acids such as hydrochloric acid, oxygen acids, such as sulphuric acid, optionally substituted benzenesulphonic acids such as benzenesulphonic acid or p-toluenesulphonic acid, or agents which split off water, such as di-lower alkyl- or dicycloalkylcarbodiimides, such as dicyclohexylcarbodiimide, or using diazo compounds such as diazo-lower alkanes, for example diazomethane, or can be converted into acid halides by treatment with suitable halogenating agents, such as thionyl halides, for example thionyl chloride, or phosphorous halides or oxyhaldies, for example phosphorus chloride or oxychloride.

Resulting esters can be hydrolysed to free acids, for example by treatment with suitable basic agents, such as aqueous alkali metal hydroxides, or can be transesterified into other esters by means of alcohols in the presence of acid or alkaline agents, such as mineral acids or complex heavy metal acids, as well as alkali metal carbonates or alkali metal alcoholates. Esters can be converted into amides by treatment with ammonia or appropriate amines.

Resulting acid halides can be converted by treatment with alcohols, as well as ammonia or amines, and resulting metal salts or ammonium salts can be converted by treatment with alcohols or appropriate halides, for example chlorides or bromides, or with thionyl halides, for example thionyl chloride, phosphorus pentoxide, phosphorus halides, for example phosphorus pentachloride, or phosphorus oxyhalides, for example phosphorous oxychloride, into esters, halides or amides, depending on the choice of the starting substances and the use of reagents.

Resulting amides can be hydrolysed under acid or alkaline conditions, for example by treatment with aqueous mineral acids and/or carboxylic acids or alkali metal hydroxides, and can also be alcoholised or transaminated.

Resulting salts or esters in which $R_3$ represents hydrogen, can be alkylated, in the $\alpha$-position to the functionally modified carboxyl group, by means of a reactive ester of a lower alkanol. Reactive esters of lower alkanols are, for example, those with strong acids, such as hydrogen halide acids, such as hydriodic acid or hydrobromic acid, oxygen acids, such as sulphuric acid, or strong organic, for example aliphatic or aromatic, sulphonic acids, such as optionally halogen-substituted lower alkanesulphonic acids, for example methanesulphonic acid or trifluoromethanesulphonic or trichloromethanesulphonic acid, or with benzenesulphonic acids which are optionally substituted, for example by lower alkyl, for example methyl, phenyl, nitro or halogen, for example chlorine or bromine, for example benezenesulphonic acid, p-toluenesulphonic acid, p-biphenylsulphonic acid, p-nitrobenzenesulphonic acid or p-bromobenzenesulphonic acid.

The alkylation is advantageously carried out in the presence of a base, such as of an alcoholate, for example an alkali metal lower alkanolate, for example sodium ethylate or potassium tert.-butylate, an alkali metal amide or alkali metal hydride, such as sodium amide or sodium hydride, an alkali metal amide derived from a secondary amine, for example an alkali metal di-lower alkylamide, such as lithium diisopropylamide, or an organic alkali metal compound, for example triphenylmethyl-sodium, and also a strong organic nitrogen-containing base, such as a tetra-lower alkylammonium lower alkanolate, such as tetra-n-butylammonium methylate.

The reaction is advantageously carried out in the presence of an organic solvent, in the case of lower alkanolates preferably in the corresponding lower alkanols, and in the case of the other bases which have been mentioned, for example, in ether-like liquids, such as in di-lower alkyl ethers, for example diethyl ether, in ethylene glycol di-lower alkyl ethers, such as ethylene glycol dimethyl ether, cyclic ethers, such as tetrahydrofurane or dioxane, hydrocarbons, such as benzene or toluene, di-lower alkylamides of lower alkanoic acids, such as dimethylformamide or dimethylacetamide, and sulphoxides, for example di-lower alkylsulphoxides, such as dimethylsulphoxide. The direct alkylation is advantageously carried out at temperatures between 0° and 120°C.

Resulting compounds can be halogenated in the aromatic radical Ar, for example using halogen, preferably in the presence of a Lewis acid, for example an iron-III halide, aluminium halide, antimony-III halide or tin-IV halide, or using a halogenating agent, for example hydrochloric acid in the presence of hydrogen peroxide, or of an alkali metal chlorate, for example sodium chlorate, a nitrosyl halide, for example nitrosyl chloride or nitrosyl bromide, or a halogeno-, for example bromo-succinimide or -phthalimide.

It is furthermore possible to introduce a nitro group into the aromatic radical Ar, for example by treatment with nitric acid or with nitrate salts under acid conditions, for example in the presence of sulphuric acid or trifluoroacetic acid. In a resulting nitro compound, the nitro group can be reduced to the amino group, for example by treatment with catalytically activated hydrogen or with chemical reducing agents (nascent hydrogen).

Resulting compounds with a primary amino group can be reacted with reactive esters of alcohols or glycols, and with reactive functional derivatives, such as halides, for example chlorides, or anhydrides or acids, and can thus be converted into compounds with secondary or tertiary amino groups or with quaternary ammonium groups, and into acylated amino groups. When treated with nitrous acid, resulting compounds with a free amino group yield diazonium salts, which can be converted into the corresponding hydroxy, halogen or lower alkoxy compounds by the Sandmeyer reaction, for example by hydrolysis at elevated temperatures, treatment with copper-II halides or with a lower alkanol, preferably under neutral or slightly acid or alkaline conditions.

In resulting phenolic products, phenolic hydroxyl groups can be etherified, for example using the corresponding metal phenolates or alkali metal phenolates, by treatment with reactive esters of lower alkanols, such as lower alkyl halides, lower alkyl sulphates or lower alkyl sulphonates, as well as by using diazo compounds, such as diazo-lower alkanes. Resulting phenol ethers can be split, for example by treatment with strong acids or acid salts, such as hydrobromic acid and acetic acid, as well as pyridine hydrochloride.

A resulting free acid can be converted into a salt in a manner which is in itself known, for example by reaction with an approximately stoichiometric amount of a suitable salt-forming agent, such as ammonia, an amine or an alkali metal or alkaline earth metal hydroxide, carbonate or bicarbonate. Ammonium salts or metal salts obtainable in this way can be converted into the free acid by treatment with an acid, for example hydrochloric acid, sulphuric acid or acetic acid, until the requisite pH value is reached.

A basic compound obtained can be converted into an acid addition salt, for example by reaction with an inorganic or organic acid or an appropriate anion exchanger and isolation of the salt formed. A resulting acid addition salt can be converted into the free compound by treatment with a base, for example an alkali metal hydroxide, ammonia or a hydroxyl ion exchanger.

The salts can also be used for the purification and identification of the free compounds; thus, free compounds can be converted into their salts, there can be isolated from the crude mixture, and the free compounds can then be obtained from the isolated salts. In view of the close relationships between the new compounds in the free from and in the form of their salts the free compounds or the salts are to be understood, in the preceding and following text, where appropriate to include the corresponding salts or free compounds, in general sense and intended use.

Resulting isomer mixtures can be separated into the individual isomers in a manner which is in itself known, for example by fractional distillation or crystallisation and/or by chromatography. Racemic products can be separated into the optical antipodes, for example by separation, such as fractional crystallisation, of mixtures of diastereoisomeric salts, for example with d- or l-tartaric acid, or with d-$\alpha$-phenylethylamine, d-$\alpha$-(1-naphthyl)-ethylamine or l-cinchonidine and, if desired, liberation of the free antipodes form the salts.

The above reactions are carried out in accordance with methods which are in themselves known, for example in the absence or presence of diluents, preferably those which are inert towards reactants and are capable of dissolving them, if necessary in the presence of catalysts, condensation agents or neutralising agents, in an inert gas atmosphere, for example nitrogen atmosphere, whilst cooling or warming and/or under elevated pressure.

The invention also relates to those modifications of the above process according to which a compound formed has an intermediate product at any stage is used as the starting material and the remaining stage or stages is or are carried out therewith, or the process is interrupted at any stage, or according to which starting substances are formed under the reaction conditions or are used in the form of salts or reactive derivatives.

The new compounds of the present invention can be administered perorally, rectally or parenterally. Suitable unit dosage forms, such as dragees, tablets, suppositories or ampoules, preferably contain, as the active substance, 10–500 mg of a compound of the formula I or of a salt of a free acid falling under this formula with a pharmaceutically tolerated inorganic or organic base. In unit dosage forms for peroral use, the content of active substance is preferably between 10% and 90%. To manufacture such unit dosage forms, the active substance is combined, for example, with solid, pulverulent excipients, such as lactose, sucrose, sorbitol or mannitol; starches, such as potato starch, corn starch or amylopectin, and also laminaria powder or citrus pulp powder; cellulose derivatives or gelatine, optionally with the addition of lubricants, such as magnesium stearate or calcium stearate or polyethylene glycols, to give tablets or to give dragee cores. The latter are coated, for example, with concentrated sugar solutions which can, for example, additionally contain gum arabic, talc and/or titanium dioxide, or with a lacquer dissolved in easily volatile organic solvents or solvent mixtures. Dyestuffs can be added to these coatings, for example to characterise various doses of active compounds. Further suitable oral unit dosage forms are push-fit capsules of gelatine as well as soft, sealed capsules of gelatine and a plasticiser, such as glycerine. The former preferably contain the active compound as granules mixed with lubricants, such as talc or magnesium stearate, and optionally with stabilisers, such as sodium metabisulphite ($Na_2S_2O_5$) or ascorbic acid. In soft capsules, the active substance is preferably dissolved or suspended in suitable liquids, such as liquid polyethylene glycols, and again stabilisers can be added. Possible unit dosage forms for rectal use are, for example, suppositories which consist of a combination or an active compound with a suppository base composition based on natural or synthetic triglycerides (for example cacao butter), polyethylene glycols or suitable higher fatty alcohols, and gelatine rectal capsules which contain a combination of the active compound with polyethylene glycols.

Ampoule solutions for parenteral, especially intramuscular or intravenous, administration contain, for example, a compound of the general formula I in a concentration of, preferably, 0.5–5%, as an aqueous dispersion prepared with the aid of customary solubilising agents and/or emulsifiers and, optionally, stabilisers, or an aqueous solution of a pharmaceutically tolerated water-soluble salt of a free acid falling under the general formula I.

Further possible forms for parenteral administration are lotions, tinctures and ointments for percutaneous administration, prepared with the usual auxiliaries.

The instructions which follow are intended to explain in more detail the manufacture of tablets and dragees:

a. 1,000 g of active substance, for example 2-phenyl-6-quinolineacetic acid are mixed with 550 g of lactose and 292 g of potato starch, and the mixture is moistened with an alcoholic solution of 8 g of gelatine and granulated through a sieve. After drying, 60 g of potato starch, 60 g of talc and 10 g of magnesium stearate and 20 g of highly disperse silica are mixed in and the mixture is pressed to give 10,000 tablets each weighing 200 mg and each containing 100 mg of active substance, the tablets being provided with breaking grooves, if desired, for more accurate selection of the dosage.

b. 200 g of active substance, for example 60-methyl-2-(p-chlorophenyl)-6-quinolineacetic acid, are well mixed with 16 g of corn starch and 6 g of highly disperse silicon dioxide. The mixture is moistened with a solution of 2 g of stearic acid, 6 g of ethyl cellulose and 6 g of stearin in approx. 70 ml of isopropyl alcohol and is granulated through a III sieve (Ph. Helv.V). The granules are dried for approx. 14 hours and then beaten through a IIIa sieve. Thereafter they are mixed with 16 g of talc and 18 g of magnesium stearate and pressed to give 1,000 dragee cores. These are coated with a concentrated syrup of 2 g of shellac, 7.5 g of gum arabic, 0.15 g of dyestuff, 2 g of highly disperse silicon dioxide, 25 g of talc and 53.35 g of sugar and are dried. The resulting dragees each weigh 360 mg and each contain 200 mg of active substance.

c. 50.0 of α-methyl-2-phenyl-6-quinolineacetic acid are dissolved in a mixture of 180 ml of 1 N sodium hydroxide solution and 500 ml of boiled pyrogen-free water and the solution is made up to 2,000 ml with the same type of water. The solution is filled into 1,000 ampoules each holding 2 ml, and is sterilised. One ampoule holding 2 ml contains 50 mg of active substance in the form of the sodium salt.

d. 50 g of α-methyl-2-(p-chlorophenyl)-6-quinolineacetic acid methyl ester and 1,950 g of finely ground suppository base composition (for example cacao butter) are thoroughly mixed and then fused. 1,000 suppositories weighing 2.0 g each are cast from the melt, which is kept homogeneous by stirring. The suppositories each contain 50 mg of active substance.

e. 60.0 of polyoxyethylene-sorbitane monostearate, 30.0 g of sorbitane stearate, 150.0 g of paraffin oil and 120.0 g of stearyl alcohol are fused together, 50.0 g of α-methyl-2-phenyl-6-quinolineacetic acid (finely powdered) are added and 590 ml of water prewarmed to 40° are emulsified in the mixture. The emulsion is stirred until it has cooled to room temperature and is filled into tubes.

The starting materials of the formula II are new and can be obtained in a manner which is in itself known, for example as follows:

An aniline derivative of the formula

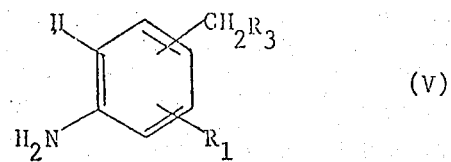

(V)

can be reacted with a compound of the formula Ar—CH=C($R_2'$)—C($R_2''$)=O (IVa) by the Doebner-Miller method in accordance with the reaction conditions described earlier. It is, however, also possible to condense a compound of the formula

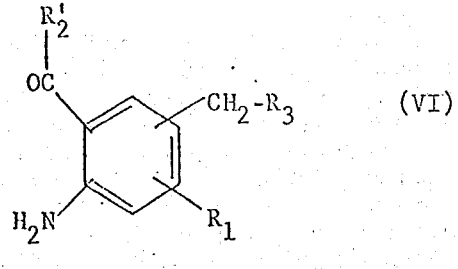

(VI)

with a ketone of the formula Ar—C(=O)—$CH_2$—$R_2''$ (IVb) according to Friedlander, under the reaction conditions described earlier. In both cases starting substances of the formula II, wherein X represents a radical of the formula —$CH_2$—$R_3$, are obtained.

In compounds of the formula II, wherein X represents a radical of the formula —$CH_2$—$R_3$, the latter can be halogenated, preferably brominated or chlorinated, in the α-position in a manner which is in itself known, whereby compounds of the formula II are obtained, wherein X represents a group of the formula —CH(R$_3$)—Hal, wherein Hal denotes a halogen, preferably a chlorine or bromine atom. Halogenation is carried out, for example, with elementary halogen, such as chlorine or bromine, or with halogen derivatives which can donate halogen radicals, such as with N-halogenoamides, for example N-bromosuccinimide or N-chlorosuccinimide, or N-bromoacetamide. The raction is advantageously initiated by the formation of radicals, with radicals being formed by irradiating the reaction mixture with light, advantageously in the ultraviolet range, or by the addition of radical-forming agents, advantageously or organic peroxides, such as optionally substituted benzoyl peroxides, for example benzoyl peroxide or an optionally substituted perbenzoic acid, for example perbenzoic acid or 3-chloroperbenzoic acid. The radical-forming agents are preferably employed in catalytic amounts.

The halogenation can be carried out in the absence of a solvent; advantageously, however, an inert solvent is used, for example a chlorinated hydrocarbon, such as carbon tetrachloride, chloroform or methylene chloride, or a lower alkane-carboxlic acid, such as acetic acid. The halogenation is advantageously carried out at normal or elevated temperature, for example between 20° and 120°C.

The halogen derivatives thus obtainable can be converted, by treatment with hydrocyanic acid or a salt thereof, for example with an alkali metal cyanide, such as sodium cyanide or potassium cyanide, into the nitriles to be used as starting substances of the formula II. The introduction of the nitrile group is advantageously carried out in a polar solvent which is inert under the reaction conditions, for example in water, a lower alkanol, such as ethanol, or, advantageously, in a liquid amide, such as dimethylformamide or dimethylacetamide, or in a sulphoxide, such as dimethylsulphoxide. The reaction is carried out at normal temperature or at elevated temperature, for example at between about 20° and 120°C.

Nitriles of the formula II, wherein $R_3$ denotes a hydrogen atom can be alkylated in the $\alpha$-position, in particular by direct alkylation or, advantageously, by indirect alkylation with a reactive ester of a lower alkanol. The direct alkylation is advantageously carried out under conditions which are described eariler in connection with the $\alpha$-alkylation of compounds of the formula I.

For the indirect alkylation, a nitrile of the formula II, wherein $R_3$ represents hydrogen, is first reacted with a carbonic acid ester, for example with a carbonic acid di-lower alkyl ester, such as carbonic acid diethyl ester, in the presence of a base, and the nitrile acylated in the $\alpha$-position is alkylated in accordance with the alkylation process described above, by treatment with a reactive ester of a lower alkanol. The resulting carboxylic acid ester is then saponified, for example by treatment with aqueous alkali, for example an aqueous alkali metal hydroxide, such as sodium hydroxide, after which the resulting $\alpha$-cyanocarboxylic acid compound is decarboxylated to give a nitrile falling under the formula II. The decarboxylation is most cases already takes place under the saponification conditions but does so reliably on further warming, for example in the same solution. The resulting nitrile does not have to be isolated but can be converted in situ into the compounds of the present invention.

The imidoesters or thioimidoesters falling under the formula II can be obtained, for example, from the nitriles falling under the formula II by the successvie action of a strong acid, preferably a hydrogen halide acid, such as hydrochloric acid, and an alcohol or mercaptan, preferably a lower alkanol. The reaction is advantageously carried out in the presence of an inert solvent, for example of one of the ether-like solvents described above, at normal or elevated temperature, say between 20° and 120°C.

Compounds of the formula II wherein $X_1$ denotes a trihalogenomethyl group, preferably a trichloromethyl group, are obtained, for example, if a diazonium salt, manufactured from an amine of the formula II, wherein X represents the amino group, is reacted with a compound of the formula $R_3—CH=C(Hal)_2$ (VII), in which Hal denotes halogen, preferably chlorine, advantageously in the presence of a copper salt, for example a copper halide, such as copper chloride, in water, or preferably in a mixture of water and an inert water-miscible organic solvent, such as a lower alkyl ketone, for example acetone, a lower alkanonitrile, such as acetonitrile, a lower alkanol, such as ethanol, or one of the water-soluble ether-like solvents described above, for example dioxane. The reaction is carried out at lowered or elevated temperature, for example between about 0° and 100°C. According to an advantageous form of carrying out the process, the diazonium salt is manufactured in the usual manner from the amino compound with sodium nitrite in aqueous hydrochloric acid, the copper salt is added, a solution of the compound of the formula VII in acetone is gradually added to the solution obtained, at about 0°, and the temperature is slowly raised from 0° to 50°C.

The compounds of the formula II, wherein $X_1$ denotes a tri-lower alkoxymethyl group are obtained, for example, by alcoholysis from the trihalogenomethyl compounds and alkali lower alkanolates, such as sodium methylate, preferably in the corresponding lower alkanol as the solvent.

The amines of the formula II, wherein X represents the amino group, are obtained, for example, by reduction of the corresponding nitro compounds, for example with hydrogen which has been activated catalytically, for example with palladium on charcoal. The nitro compounds can in turn be manufactured, for example, from corresponding nitroanil compounds in accordance with the methods of synthesis of quinoline indicated above.

Thioamides falling under the formula II can be manufactured from the corresponding nitriles by the action of hydrogen sulphide or phosphorus pentasulphide, and also from compounds of the formula II, wherein X represents an acetyl group, by the methods of Willgerodt or Willgerodt-Kindler, by treating with ammonium polysulphide or with ammonia or a primary or a secondary amine and sulphur. The reaction with ammonium polysulphide is carried out, for example, in a medium wherein one or preferably both reactants are at least partially soluble, for example dioxane, in a closed vessel at temperatures of around 160°–220°. According to the Kindler modification, the reaction can be carried out, for example, with aqueous or anhydrous ammonia or with a mono- or di-lower alkylamine, such as diethylamine, or an alkyleneamine, such as piperidine, and with sulphur, again in a closed vessel and if appropriate in the presence of pyridine at temperatures of about 140°C to about 180°C. According to the customary embodiment of the Kindler modification, morpholine, of which the boiling point of 138°C renders the use of pressure vessels superfluous, is used as the amine. For example, a mixture of a compound of the formula II, wherein X represents an acetyl group, and of sulphur in excess morpholine is boiled under reflux, whereupon a corresponding thioacetic acid morpholide of the formula II is formed.

The ketones of the formula II, wherein X denotes an acetyl group, which are used as intermediate products are obtained, for example, by oxidation of a compound of the formula II, wherein X denotes an ethyl group. The oxidation can, for example, be effected by treatment with selenium dioxide in the presence of an organic solvent, for example in an ether-like solvent, such as dioxane, at an elevated temperature, for example at the reflux temperature.

The manufacture of the organo-metallic compounds of the formula II, wherein X represents a group of the formula $-CH(R_3)-X_2$ (IIc), in which $X_2$ denotes a metallic radical, these compounds being used as starting substances, advantageously starts from halogen compounds of the formula II, wherein X represents a group of the formula $-CH(R_3)-Hal$, which are reacted with one of the abovementioned metals, preferably with lithium or magnesium. It is, however, also possible to react an appropriate halogen compound with an organo-metallic compound, preferably with a lower alkyl-lithium or lower alkyl-magnesium halide, for example butyl-lithium, or with an aryl-lithium or aryl-magnesium halide, such as phenyl-lithium. The manufacture of the above organo-metallic compounds, which are advantageously not isolated, is preferably carried out in the solvents described for the further reaction, and at the same temperatures.

The starting material of the formula II used above, wherein X is a group of the formula $-CH(R_3)-X_3$ (IId), wherein $X_3$ represents an optionally etherified hydroxyl group, can be obtained, for example, from a compound of the formula II, wherein X represents a radical of the formula $-CH(R_3)-Hal$, by hydrolysis or alcoholysis, preferably under alkaline conditions, for example by treatment with the abovementioned basic reagents, such as an aqueous-alcoholic solution of an alkali metal hydroxide, such as sodium hydroxide, or with an alkali metal lower alkanolate in a lower alkanol, working, for example at between about 20° and 100°C.

The manufacture of the above aldehydes of the formula II used as starting materials, wherein X represents a group of the formula $-CH(R_3)-CHO$ (IIe), starts, for example, from an organo-metallic compound of the formula II, wherein X is the group of the formula IIc, which is allowed to react with a reactive functional derivative of formic acid, preferably with a formic acid ester, such as one of the abovementioned formic acid lower alkyl esters, or with a suitable substituted 2-oxazolinium salt, such as N,4,4-trimethyl-2-oxazolinium iodide.

The starting substances of the formula II, wherein X represents a group of the formula IIg, can be obtained, for example, by condensation of a compound of the formula II, wherein X represents a group of the formula IIb, in which $R_3$ denotes hydrogen and $X_1$ denotes the nitrile group, with an aldehyde or ketone of the formula $R_3°=O$ (VIII). The condensation is carried out, for example, under the reaction conditions described for the alkylation of the corresponding nitriles. The resulting α-lower alkylidene-substituted nitriles can be converted into the corresponding acids, or into their esters or amides, as described above.

The above starting materials of the formula II, wherein X denotes the group of the formula IIh or of the formula IIi, can be manufactured, for example, from the corresponding functional derivatives with regard to the free carboxyl group, preferably from the esters, especially the lower alkyl esters or benzyl esters, for example by hydrolysis or hydrogenolysis, it also being possible to prepare the acids, used as starting substances, in situ.

The functional derivatives of the compounds of the formula II, wherein X denotes the group of the formula IIh or IIi, can be manufactured, for example, by acylation of compounds of the formula II, wherein X represents a radical of the formula IIb, wherein $X_1$ is a nitrile group, with a carbonic acid derivative or an oxalic acid derivative, preferably with an ester, such as a lower alkyl ester or benzyl ester, for example with diethyl carbonate, dibenzyl carbonate, oxalic acid diethyl ester or oxalic acid dibenzyl ester, in the presence of a base, with subsequent saponification of the nitrile group.

The starting substances of the formula II, wherein X represents a group of the formula $-C(=O)-C(N_2)-R_3$ (IIk), can be obtained by treating a compound of the formula II, wherein X represents a halogenocarbonyl group, for example a chlorocarbonyl group, with a diazoalkane of the formula $R_3-CH=N=N$, preferably in the presence of a solvent, for example one of the ether-like solvents described above, or a hydrocarbon, at a temperature of about −10° to about 140°C.

The acid halides used in the above manufacture of the starting substances can be obtained, for example, from the corresponding acids, for example by treatment with a thionyl halide, such as thionyl chloride.

Starting materials of the formula III, wherein $Z_1$ is hydrogen, are known or can be manufactured analogously to known compounds.

The starting materials of the formula IIIb can be manufactured in a manner which is in itself known. However, they are advantageously manufactured in situ by reaction of an aniline of the formula III, wherein $Z_1$ denotes hydrogen, with a carboxylic acid, such as formic acid or acetic acid, or a reactive functional derivative thereof, for example with a formic acid lower alkyl ester, such as formic acid ethyl ester, or with acetic anhydride, preferably in the presence of one of the above acid catalysts. In this reaction variant, for example, an aniline of the formula III is heated with formic acid to a temperature of above 100°, the compound of the formula IV, wherein $Z_2$ is a group of the formula IVb, such as the acetyl group, and, preferably, a condensation agent, such as, for example, zinc-chloride, are then added, and the mixture is further warmed to about 200° until the condensation is complete.

The examples which follow explain the manufacture of the new compounds according to the invention in more detail but are not intended to restrict the scope of the invention in any way.

EXAMPLE 1

A mixture of 10 g of 2-phenyl-6-quinolineacetonitrile, 19 ml of water, 19 ml of concentrated sulphuric acid and 19 ml of glacial acetic acid is kept under reflux for 2 hours. Thereafter, ice and water are added and the pH is adjusted to 5–6 with solid sodium bicarbonate. The crystals which thereupon precipitate are filtered off and rinsed with water. Recrystallisation from methanol-ether-petroleum ether yields 2-phenyl-6-quinolineacetic acid of melting point 176°–179°C. 2-(p-Chlorophenyl)-6-quinoline-acetic acid and 2-(p-fluorophenyl)-6-quinolineacetic acid are obtained analogously.

The 2-phenyl-6-quinolineacetonitrile used as the starting material is manufactured as follows:

a. A mixture of 400 g of p-toluidine, 171 g of formic acid and 253 g of zinc chloride is stirred for 4 hours under reflux at a bath temperature of 150°–160°C. It is cooled to 100°C, 224 g of acetophenone are rapidly added dropwise and the reaction mixture is stirred for 20 hours at a bath temperature of 180°–190°C, whilst distilling off a part of the formic acid through a distillation elbow. Thereafter the reaction mixture is cooled to 100°C, 600 ml of a 1:1 mixture of chloroform and ethyl acetate are added and the mixture is boiled under reflux until it can again be stirred easily. The suspension is cooled and the crystals which have precipitated are filtered off and thoroughly rinsed with chloroform-ethyl acetate, 1:1, until the filter residue is white. The filtrate is evaporated and the residue is dissolved in ethyl acetate. This solution is washed three times with concentrated ammonia and then evaporated on a rotary evaporator, and the residue is steam-distilled. The residue from the steam distillation is extracted with ethyl acetate and the organic phases are then separated off and extracted with 4 times 400 ml of 5 N hydrochloric acid. The hydrochloric acid extracts are adjusted to pH 8–9 and extracted with ethyl acetate. The organic phases are washed with sodium chloride solution, dried over sodium sulphate, combined and concentrated. Hereupon 2-phenyl-6-methyl-quinoline crystallises out. Melting point 64°–65°C (from methanol).

Analogously, toluidine and p-fluoroacetophenone yield 2-(p-fluorophenyl)-6-methyl-quinoline, melting point 106°–107°C (from ethanol-water), and toluidine and p-chloroacetophenone yield 2-(p-chlorophenyl)-6-methyl-quinoline, melting point 154°–155°C (from ethanol-ether).

b. A solution of 54 g of 2-phenyl-6-methyl-quinoline, 68 g of N-bromosuccinimide and 1.5 g of dibenzoyl peroxide in 700 ml of carbon tetrachloride is kept for 18 hours under reflux. Thereafter the reaction mixture is cooled to room temperature and the precipitate is filtered off. The filter residue is rinsed with carbon tetrachloride. The filtrate is evaporated and the residue is dissolved in ethyl acetate. This solution is washed with water and sodium chloride solution, dried over sodium sulphate and evaporated. The residue is taken up in 1.8 litres of ether and the insoluble constituents are filtered off. Concentration of the solution yields 2-phenyl-6-bromomethyl-quinoline of melting point 126°–127°C.

Analogously, 2-(p-chlorophenyl)-6-methylquinoline yields 2-(p-chlorophenyl)-6-bromomethyl-quinoline of melting point 123°–126°C (from carbon tetrachloride) and 2-(p-fluorophenyl)-6-methylquinoline yields 2-(p-fluorophenyl)-6-bromomethyl-quinoline of melting point 117°–118°C (from carbon tetrachloride).

A solution of 6 g of 2-phenyl-6-bromomethyl-quinoline and 3 g of sodium cyanide in 60 ml of dimethylsulphoxide is stirred for 4 hours at 40°C. Thereafter 500 ml of ice water are added and the product which hereupon precipitates is filtered off. When the filter residue is recrystallised from 200 ml of ethanol, 2-phenyl-6-quinolineacetonitrile of melting point 159°–161°C is obtained.

The following products are obtained analogously, the crystallisation being preceded, in some cases, by a chromatography:

2-(p-Chlorophenyl)-6-quinolineacetonitrile, melting point 159°–160°C (from chloroform/petroleum ether).

2-(p-Fluorophenyl)-6-quinolineacetonitrile of melting point 139°–140°C (from chloroform/petroleum ether).

EXAMPLE 2

A mixture of 11 g of α-methyl-2-phenyl-6-quinolineacetonitrile, 23 ml of water, 23 ml of glacial acetic acid and 23 ml of concentrated sulphuric acid is boiled under reflux for 8 hours. The reaction mixture is cooled, treated with ice water and adjusted to pH 8 with 2 N sodium carbonate solution. This solution is treated with active charcoal, warmed on a water bath for 1 hour and then filtered. The filtrate is adjusted to pH 5 with concentrated hydrochloric acid and the precipitate which hereupon separates out is filtered off and rinsed with water. After recrystallisation from ethanol-water, α-methyl-2-phenyl-6-quinolineacetic acid of melting point 161°–162°C are obtained.

The following are obtained analogously:

α-Methyl-2-(p-chlorophenyl)-6-quinolineacetic acid of melting point 189°–190°C (from ethyl acetate-petroleum ether).

α-Methyl-2-(p-fluorophenyl)-6-quinolineacetic acid of melting point 179°–180°C (from ethyl acetate-petroleum ether).

α-Methyl-2-(2-thienyl)-6-quinolineacetic acid of melting point 171°–173°C (from chloroform).

The α-methyl-2-phenyl-6-quinolineacetonitrile used as the starting material is obtained as follows:

a. 12 g of 2-phenyl-6-quinolineacetonitrile are added at 60°C, whilst stirring, to a dispersion prepared from 2.6 g of sodium hydride dispersion (50% strength) in 50 ml of toluene. 90 ml of dimethyl carbonate are now added and the mixture is distilled dropwise at a heating bath temperature of 160°–170°C until the boiling point rises to 93°C. A further 90 ml of dimethyl carbonate are added and the mixture is again distilled until the excess dimethyl carbonate has been removed (the boiling point rises to above 92°C). After cooling, the solid residue is treated with 40 ml of toluene and 60 ml of dimethyl-formamide. Immediately, 9 ml of methyl iodide are also added and the reaction mixture is stirred for 18 hours at room temperature. Thereafter the reaction mixture is poured onto 800 ml of ice water and the suspension is well stirred and treated with a little ether. Hereupon, α-cyano-α-methyl-2-phenyl-6-quinolineacetic acid methyl ester, melting at 133°–134°C after drying, crystallises out. Further product can be obtained from the aqueous phase by extraction with ethyl acetate and evaporation of the organic solution.

The following are obtained analogously: α-cyano-α-methyl-2-(p-chlorophenyl)-6-quinolineacetic acid methyl ester, α-cyano-α-methyl-2-(p-fluorophenyl)-6-quinolineacetic acid methyl ester and α-cyano-α-methyl-2-(2-thienyl)-6-quinolineacetic acid methyl ester; they are further processed in the crude state.

b. 36.4 ml of 1 N sodium hydroxide solution are added dropwise to a solution of 10.4 g of α-cyano-α-methyl-2-phenyl-6-quinolineacetic acid methyl ester in 580 ml of ethanol at room temperature. The reaction mixture is stirred for 16 hours at room temperature and evaporated to dryness, the residue is treated with water and the suspension thereby produced is filtered off. After drying in vacuo at 40°C, crude α-methyl-2-phenyl-6-quinolineacetonitrile is obtained, which is directly processed further.

The following are obtained analogously: α-methyl-2-(p-chlorophenyl)-6-quinolineacetonitrile of melting point 126°C (from ethanol), α-methyl-2-(p-fluorophenyl)-6-quinoline-acetonitrile of melting point 126°–128°C (from ethanol) and crude α-methyl-2-(2-thienyl)-6-quinolineacetonitrile.

EXAMPLE 3

A mixture of 3 g of 2-(2-thienyl)-6-quinolineacetonitrile, 8.6 ml of water, 8.6 ml of glacial acetic acid and 8.6 ml of concentrated sulphuric acid is boiled for 3 hours under reflux. Thereafter the reaction mixture is cooled, treated with ice water and adjusted to pH 5–6 with solid sodium bicarbonate. The resulting suspension is extracted with ethyl acetate and the organic phases are washed with water, dried over sodium sulphate and evaporated. The residue obtained is 2-(2-thienyl)-6-quinolineacetic acid, the melting point of which, after recrystallisation from acetone-petroleum ether, is about 172°C.

The 2-(2-thienyl)-6-quinolineacetonitrile used as the starting material is obtained as follows:

a. 34 g of zinc chloride are added to a mixture of 53.6 g of p-toluidine and 24 g of formic acid. The mixture is stirred for 3 hours under reflux. Thereafter the reflux condenser is replaced by a distillation elbow, 31.5 g of 2-acetylthiophene are added to the reaction mixture and the mixture is stirred for 30 hours at a heating bath temperature of 180°–200°C, in the course of which formic acid distils off. Thereafter the mixture is cooled to 100°C, a mixture of 100 ml of chloroform and 100 ml of ethyl acetate is added and the whole is stirred for 30 minutes under reflux, whereby a suspension is produced. This is filtered and the residue is rinsed with ethyl acetate-chloroform. The filtrate is washed three times with concentrated aqueous ammonia solution and with water and is dried over sodium sulphate and evaporated. The residue is chromatographed on silica gel. 2-(2-Thienyl)-6-methyl-quinoline is eluted with a mixture of petroleum ether and methylene chloride in the ratio of 1:1; after recrystallisation from ether/petroleum ether/pentane, it melts at 116°C.

b. 11.9 g of 2-(2-thienyl)-6-methyl-quinoline together with 360 ml of carbon tetrachloride, 10.4 g of N-bromosuccinimide and 0.3 g of dibenzoyl peroxide are boiled for 15 hours under reflux. The reaction mixture is cooled and filtered off. Concentration of the filtrate yields 2-(2-thienyl)-6-bromomethyl-quinoline which melts at 95°C.

c. A solution of 14 g of 2-(2-thienyl)-6-bromomethyl-quinoline in 150 ml of dimethylsulphoxide is treated with 3.6 g of sodium cyanide. The reaction mixture is stirred for 40 minutes at 30°–40°C and subsequently for a further 30 minutes at room temperature. Thereafter it is poured onto 500 g of ice. After thorough stirring, the product separates out as a precipitate. This is separated off and purified by chromatography on silica gel. 2-(2-Thienyl)-6-quinolineacetonitrile is eluted with toluene; after recrystallisation from chloroform-ether-pentane, it melts at 157°C.

EXAMPLE 4

45 ml of cinnamaldehyde are added dropwise to a mixture of 38 g of p-aminophenylacetic acid, 71 g of arsenic acid and 300 ml of phosphoric acid. The reaction mixture is stirred for 2 hours at 120°C, 50 ml of polyphosphoric acid are then added and the whole is again stirred for 16 hours at 110°–120°C. The reaction mixture is cooled to 0°C and adjusted to a pH of 5–6 first with 2 N sodium hydroxide solution and then with solid sodium carbonate. This suspension is extracted with ethyl acetate and the organic phases are then extracted 6 times with 50 ml of 1 N hydrochloric acid at a time. The hydrochloric extracts are combined and a few pinches of sodium nitrite are added. The solution is left to stand for 15 minutes at room temperature and is then adjusted to pH 5.6, using a pH-meter, by adding sodium carbonate. This solution is extracted with ethyl acetate and the organic layers are washed with water, dried over sodium sulphate and evaporated. The residue obtained is crude 2-phenyl-6-quinolineacetic acid.

Melting point 176°–179°C (from methanol-pentane). α-Methyl-2-phenyl-6-quinolineacetic acid of melting point 161°–162°C (from ethanol-water) is obtained analogously.

EXAMPLE 5

A mixture consisting of 1.9 g of α-methyl-2-(p-chlorophenyl)-6-quinolineacetic acid, 28 ml of methanol and 28 drops of concentrated sulphuric acid is kept for 2 hours under reflux. Thereafter the reaction mixture is concentrated on a rotary evaporator. The residue is treated with ice, ehter and 50 ml of 0.5 N sodium chloride solution. After thorough shaking, the aqueous phase is separated off and the organic phase is washed with water, dried over sodium sulphate and evaporated. The residue is dissolved in 25 ml of ethyl acetate and treated with petroleum ether until it crystallises. α-Methyl-2-(p-chlorophenyl)-6-quinolineacetic acid methyl ester of melting point 114°–115°C is obtained.

The following are manufactured analogously: α-Methyl-2-(2-thienyl)-6-quinolineacetic acid methyl ester.

α-Methyl-2-phenyl-6-quinolineacetic acid methyl ester of melting point 87°–89°C (from ether).

EXAMPLE 6

A mixture of 30 g of p-aminohydratropic acid methyl ester, 7.7 g of formic acid and 11.4 g of zinc chloride is stirred under reflux for 2 hours at a heating bath temperature of 160°C. Thereafter the reflux condenser is replaced by a distillation elbow. 20 g of acetophenone are added to the mixture which is stirred for 16 hours at a heating bath temperature of 200°C, in the course of which a slight amount of distillate passes over. The mixture is allowed to cool and the resulting crude α-methyl-2-phenyl-6-quinolineacetic acid methyl ester is hydrolysed as follows:

A solution of 14 g of potassium hydroxide in 26 ml of water and 260 ml of ethanol is added to the reaction mixture and the mixture is stirred, with warming, until a homogeneous suspension has formed. The white precipitate is filtered off and the filtrate is boiled under reflux for 3 hours. Thereafter the solution is evaporated to dryness. The residue is distributed between ethyl acetate and water. The aqeuous phase is treated with active charcoal, acidified to pH 6 and extracted with ethyl acetate. Drying and evaporation of the ethyl acetate solution yields crude α-methyl-2-phenyl-6-quinolineacetic acid. After further purification by chromatography and recrystallisation from ethanol-water, the melting point is 163°C.

Analogously, 2-acetylthiophene, p-amino-hydratropic acid methyl ester and formic acid yield α-methyl-2-(2-thienyl)-6-quinolineacetic acid of melting point 171°–173°C (from chloroform).

EXAMPLE 7

α-Methyl-2-phenyl-6-quinolineacetic acid (2.77 g) is dissolved in 10 ml of 1 N sodium hydroxide solution. The solution is evaporated to dryness and the residue is dissolved in isopropanol. On cooling the solution, the sodium salt of α-methyl-2-phenyl-6-quinolineacetic acid, of melting point 275°–276°C, crystallises out.

EXAMPLE 8

A solution of 1.9 g of 2-phenyl-6-quinolinecarboxylic acid (v. Braun, Ber. 60, 1,255) in 20 ml of methylene chloride is treated with 1 g of pyridine, 0.7 g of thionyl chloride is then added and the mixture is boiled for 3 hours under reflux in a nitrogen atmosphere. After cooling, the reaction mixture is evaporated to dryness on a rotary evaporator, absolute benzene is added to the residue which is again evaporated, and this procedure is repeated until the thionyl chloride has been completely removed. The residue is treated with 20 ml of absolute tetrahydrofurane and the suspension thus obtained is added dropwise over the course of 1 hour at 0°–10°C, whilst stirring, to 70 ml of an 0.34 molar solution of diazomethane in ether, to which 15 ml of absolute dioxane have also been added. The reaction mixture is stirred for a further 10 hours at room temperature and is then evaporated on a rotary evaporator at a bath temperature of 30°C.

The residue is dissolved in 36 ml of methanol, the solution is heated to the refluxing temperature and silver oxide, obtained by reaction of 1 g of silver nitrate with 1 N sodium hydroxide solution, washing with water and with methanol, is added in portions until the evolution of gas ceases, which requires about 4 hours. Thereafter the precipitate of silver is filtered off and the filtrate is evaporated. The 2-phenyl-6-quinolineacetic acid methyl ester thereby obtained, together with 1.7 g of potassium hydroxide, 10 ml of ethanol and 1 ml of water, is kept for 3 hours under reflux and is subsequently left to stand for a further 10 hours at room temperature. The solution is filtered through glass wool, which is rinsed with ethanol, and is evaporated. The residue is dissolved in 30 ml of water and this solution is twice washed with 40 ml of ether at a time, then warmed on a water bath to remove the ether, and treated with 0.5 g of charcoal. The aqueous solution is now adjusted to a pH of 1 with concentrated hydrochloric acid and twice washed with 50 ml of ether. Thereafter it is adjusted to a pH of 5.6 with solid sodium bicarbonate and extracted with ethyl acetate. Washing, drying and evaporation of the ethyl acetate layers yields 2-phenyl-6-quinolineacetic acid which after recrystallisation from methanol-ether-petroleum ether melts at 176°–179°C.

$\alpha$-Methyl-2-phenyl-6-quinolineacetic acid of melting point 161°–162°C is manufactured analogously.

EXAMPLE 9

A solution of 2.5 g of crude 2-phenyl-6-quinolineacetaldehyde in 3 ml of ethanol is slowly added dropwise at room temperature to a suspension of 3.4 g of silver nitrate and 1.6 g of sodium hydroxide in 12 ml of water. After completion of the addition, the mixture is stirred for a further 3 hours. Thereafter the suspension is clarified by filtration and the filtrate is washed with ether and adjusted to a pH of 6. The emulsion thereby produced is extracted with ethyl acetate. The ethyl acetate extracts, after drying, evaporation and recrystallisation of the residue from methanol-pentane, yield 2-phenyl-6-quinolineacetic acid of melting point 176°–179°C.

Analogously to Example 9, 2-(2-thienyl)-6-quinolineacetaldehyde yields 2-(2-thienyl)-6-quinolineacetic acid of melting point 172°C.

The 2-phenyl-6-quinolineacetaldehyde used as the starting material is obtained as follows:

a. 6.2 g of 6-bromomethyl-2-phenyl-quinoline and magnesium in 30 ml of tetrahydrofurane are used to prepare the corresponding Grignard compound in the usual manner. 7.9 g of hexamethylphosphoramide are added to this solution and the mixture is added dropwise at room temperature, whilst stirring, to a stirred suspension of 4.8 g of N,4,4-trimethyl-2-oxazolinium iodide in 60 ml of tetrahydrofurane. The reaction mixture is stirred for a further 16 hours and is then treated with ice water and rendered acid with 2 N hydrochloric acid. The acid solution is washed with hexane, rendered alkaline with sodium hydroxide solution and extracted with ether. The ether extracts are evaporated. The residue is treated with a solution of 8 g of oxalic acid in 50 ml of water and the mixture is boiled for 15 minutes under reflux. The solution is cooled and crude 2-phenyl-6-quinolineacetaldehyde is extracted therefrom with ether; it is used in the crude form.

Analogously, 6-bromomethyl-2-(2-thienyl)-quinoline yields crude 2-(2-thienyl)-6-quinolineacetaldehyde.

EXAMPLE 10

Dried hydrochloric acid gas is passed into a solution of 25 g of 2-(p-chlorophenyl)-6-quinolineacetonitrile in 80 ml of of absolute methanol, whilst cooling with ice, until saturation is reached. Thereafter the reaction mixture is left to stand for 16 hours at room temperature and evaporated on a rotary evaporator, and the residue is treated with 200 ml of water, 400 ml of dioxane and a little ice. The pH is adjusted to 7 with solid sodium acetate. Thereafter the solution is kept for 10 minutes at 40°–50°C and evaporated, and the residue is treated with water. This suspension is twice extracted with 300 ml of ether at a time and the combined ether solutions are washed with 1 N sodium carbonate solution and with saturated sodium chloride solution, dried and concentrated to 40 ml. Thereupon, 2-(p-chlorophenyl)-6-quinolineacetic acid methyl ester of melting poont 119°–121°C crystallises out.

EXAMPLE 11

10 g of 2-(p-chlorophenyl)-$\alpha$-methyl-6-quinolinemalonic acid are heated to 190°C for 20 minutes. The melt is cooled and dissolved in ethyl acetate, and the solution is extracted with 0.5 N sodium carbonate solution. The sodium carbonate extracts are adjusted to pH 5 and extracted with ethyl acetate. The ethyl acetate extracts, on evaporation and recrystallisation of the residue from ethyl acetate-petroleum ether, yield 2-(p-chlorphenyl)-$\alpha$-methyl-6-quinolineacetic acid of melting point 188°–189°C.

$\alpha$-Methyl-2-phenyl-6-quinolineacetic acid of melting point 161°–2°C, 2-(p-fluorophenyl)-$\alpha$-methyl-6-quinolineacetic acid of melting point 179°–180°C and $\alpha$-methyl-2-(2-thienyl)-6-quinolineacetic acid of melting point 166°–167°C are obtained analogously.

The 2-(p-chlorophenyl)-$\alpha$-methyl-6-quinolinemalonic acid used as the starting material is manufactured as follows:

a. 13.9 g of 2-(p-chlorophenyl)-6-quinolineacetic acid methyl ester are added to a mixture of 2.3 g of sodium hydride dispersion and 90 ml of dimethyl carbonate. 70 ml of the dimethyl carbonate are now distilled off, a further 30 ml of dimethyl carbonate are added and this is again distilled from the reaction mixture. The suspension which remains is cooled to 0°C and 3.2 ml of methyl iodide are added. The mixture is stirred for half an hour at 0°C, a further 3.2 ml of methyl iodide are added and the mixture is further stirred for 2 hours at 60°–70°C. The reaction mixture is cooled and poured onto a mixture of 400 ml of ice water and 9 ml of 5 N hydrochloric acid. The suspension thus produced is extracted with ether and the ether phases are washed with saturated sodium chloride solution, dried, combined and evaporated. 2-(p-Chlorophenyl)-α-methyl-6-quinolinemalonic acid dimethyl ester is obtained as the residue, in the form of a yellowish oil.

b. A mixture of 16.2 g of 2-(p-chlorophenyl)-α-methyl-6-quinolinemalonic acid dimethyl ester, 160 ml of butanol, 50 ml of water and 5.6 g of potassium hydroxide is boiled for 4 hours under reflux. Thereafter the reaction mixture is evaporated to dryness, the residue is partitioned between ether and water and the aqueous layer is separated off, adjusted to a pH of 5–6 with 5 N hydrochloric acid and extracted with ethyl acetate. The ethyl acetate extracts are washed with water until neutral, dried and evaporated. The residue obtained is crude 2-(p-chlorophenyl)-α-methyl-6-quinolinemalonic acid.

The following crude products are manufactured analogously: α-methyl-2-phenyl-6-quinolinemalonic acid, β2-(p-fluorophenyl)-α-methyl-6-quinolinemalonic acid, and α-methyl-2-(2-thienyl)-6-quinolinemalonic acid.

EXAMPLE 12

The Grignard compound is prepared in the customary manner from 5 g of 6-bromomethyl-2-phenyl-quinoline and magnesium in 30 ml of diethyl ether. It is added to a solution of solid carbon dioxide in 100 ml of diethyl ether. At the same time a further quantity of solid carbon dioxide is added in portions to the reaction solution. Thereafter, aqueous ammonium chloride solution is added to the reaction mixture and the whole is extracted with ethyl acetate. The organic phases are extracted with 2 N sodium carbonate solution. The sodium carbonate extracts are adjusted to pH 6 and extracted with ethyl acetate. These ethyl acetate layers are dried and evaporated. The residue, after recrystallisation from methanol-pentane, yields 2-phenyl-6-quinolineacetic acid of melting point 176–179°C.

Analogously to Example 12, 2-(2-thienyl)-6-bromomethyl-quinoline yields 2-(2-thienyl)-6-quinolineacetic acid of melting point 172°C.

EXAMPLE 13

A mixture of 35.8 g of p-aminohydratropic acid methyl ester and 20.5 g of acetic anhydride is treated with 12 g of glacial acetic acid and 13.7 g of zinc chloride. This reaction mixture is stirred for 3 hours at 150°C. Thereafter 25.3 g of 2-acetylthiophene are added dropwise over the course of 10 minutes at 100°C, whilst stirring. The reflux condenser is replaced by a distillation elbow and the reaction mixture is stirred for a further 20 hours at 185°C. The reaction mixture is now treated with chloroform at 150°C, briefly kept under reflux and then filtered. The filter residue is additionally extracted twice with chloroform and is then partitioned between concentrated ammonia solution and ethyl acetate. The chloroform solutions and the ethyl acetate solution are combined and evaporated. The residue, crude 4,α-dimethyl-2-(2-thienyl)-6-quinolineacetic acid methyl ester, is kept for 5 hours under reflux with 22.5 g of potassium hydroxide, 600 ml of ethanol and 33.3 ml of water to produce complete saponification. The reaction mixture is evaporated, the residue is dissolved in 700 ml of water, and the aqueous solution is washed with ether and combined with the ammonia solution obtained above. The resulting solution is adjusted to pH 5 and extracted with ethyl acetate. The ethyl acetate solutions are repeatedly extracted with 1 N hydrochloric acid. The hydrochloric acid extracts are adjusted to pH 6 and extracted with ethyl acetate and the organic phases are washed with saturated sodium chloride solution, combined, dried and evaporated. The residue, after recrystallisation from methanol, yields 4,α-dimethyl-2-(2-thienyl)-quinolineacetic acid of melting point 228°–229°C.

What we claim is:

1. An anti-inflammatory or analgesic pharmaceutical composition comprising an anti-inflammatory or analgesically effective amount of a compound corresponding to the formula

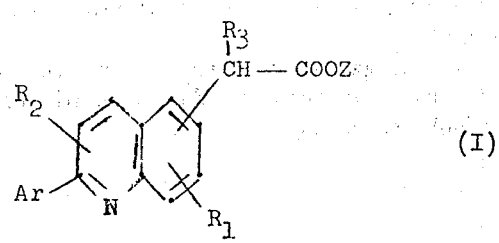

(I)

wherein Ar denotes phenyl, thienyl or phenyl substituted by one or two identical members selected from lower alkyl, lower alkoxy, fluoro, chloro, bromo, trifluoromethyl, amino, di-lower alkyl amino, or hydroxy, $R_1$ represents hydrogen, fluoro, chloro, bromo, lower alkyl, lower alkoxy or trifluoromethyl and $R_2$ and $R_3$ independently of one another denote hydrogen or lower alkyl and Z is OH, $NH_2$, OR, NHR, NRR or NHOH, where R is lower alkyl in which "lower" defines one to seven carbon atoms, or a pharmaceutically acceptable non-toxic salt thereof and a pharmaceutical carrier.

2. A composition as claimed in claim 1, in which effective compound Ar denotes phenyl, thienyl or phenyl substituted by one or two identical members selected from alkyl or alkoxy with at most 4 carbon atoms, fluorine, chlorine, bromine or tri-fluoromethyl, $R_1$ denotes hydrogen or chlorine, $R_2$ and $R_3$ independently of one another denote hydrogen or alkyl with at most 4 carbon atoms, and Z is OH, OR, $NH_2$ or NHOH where R is alkyl with at most 4 carbon atoms, and wherein one of the groups —CH($R_3$) COOZ and $R_1$ occupies the 6-position and the other the 8-position and the group $R_2$ occupies the 4-position, or a pharmaceutically acceptable non-toxic salt thereof.

3. A composition as claimed in claim 1, in which effective compound Ar denotes a phenyl, thienyl or phenyl substituted by one fluorine, chlorine, methyl, methoxy or trifluoromethyl, $R_1$ denotes hydrogen, $R_2$ denotes hydrogen or methyl in the 4-position, $R_3$ denotes hydrogen or methyl, and Z denotes OH or methoxy, and wherein the —CH($R_3$)COOZ group occupies the 6-position, or a pharmaceutically acceptable non-toxic salt thereof.

4. A composition as claimed in claim 1, in which the effective compound is the α-methyl-2-phenyl-6-quinolineacetic acid methyl ester.

5. A composition as claimed in claim 1, in which the effective compound is the α-methyl-2-(p-chlorophenyl)-6-quinolineacetic acid methyl ester.

6. A composition as claimed in claim 1, in which the effective compound is the α-methyl-2-(p-fluorophenyl)-6-quinolineacetic acid methyl ester.

7. A composition as claimed in claim 1, in which the effective compound is the α-methyl-2-(2-thienyl)-6-quinolineacetic acid methyl ester.

8. A composition as claimed in claim 1, in which the effective compound is the 2-phenyl-6-quinolineacetic acid.

9. A composition as claimed in claim 1, in which the effective compound is the 2-(p-chlorophenyl)-6-quinolineacetic acid.

10. A composition as claimed in claim 1, in which the effective compound is the 2-(p-fluorophenyl)-6-quinolineacetic acid.

11. A composition as claimed in claim 1, in which the effective compound is the 2-(2-thienyl)-6-quinolineacetic acid.

12. A composition as claimed in claim 1, in which the effective compound is the α-methyl-2-phenyl-6-quinolineacetic acid.

13. A composition as claimed in claim 1, in which the effective compound is the α-methyl-2-(p-chlorophenyl)-6-quinolineacetic acid.

14. A composition as claimed in claim 1, in which the effective compound is the α-methyl-2-(p-fluorophenyl)-6-quinolineacetic acid.

15. A composition as claimed in claim 1, in which the effective compound is the α-methyl-2-(2-thienyl)-6-quinolineacetic acid.

16. A composition as claimed in claim 1, in which the effective compound is the 4,α-dimethyl-2-(2-thienyl)-6-quinolineacetic acid.

17. The method of producing an anti-inflammatory effect in a mammal which comprises administering to said mammal an anti-inflammatory effective amount of a composition according to claim 1.

18. The method of producing an anti-nociceptive effect in a mammal which comprises administering to said mammal an analgetically effective amount of a composition according to claim 1.

* * * * *